United States Patent [19]

Gers-Barlag et al.

[11] Patent Number: 6,080,388
[45] Date of Patent: Jun. 27, 2000

[54] COSMETIC AND DERMATOLOGICAL SUNSCREEN FORMULATIONS CONTAINING TRIAZINE DERIVATIVES AND ALKANE CARBOXYLIC ACIDS

[75] Inventors: Heinrich Gers-Barlag; Rainer Kropke, both of Hamburg, Germany

[73] Assignee: Beiersdorf AG, Hamburg, Germany

[21] Appl. No.: 09/101,115

[22] PCT Filed: Jan. 6, 1997

[86] PCT No.: PCT/EP97/00029

§ 371 Date: Jan. 25, 1999

§ 102(e) Date: Jan. 25, 1999

[87] PCT Pub. No.: WO97/25020

PCT Pub. Date: Jul. 17, 1997

[30] Foreign Application Priority Data

Jan. 13, 1996 [DE] Germany .............. 196 01 104

[51] Int. Cl.[7] .............. A61K 7/44; A61K 7/42; A61K 7/00

[52] U.S. Cl. .............. 424/60; 424/59; 424/400; 424/401

[58] Field of Search .............. 424/59, 60, 400, 424/401

[56] References Cited

FOREIGN PATENT DOCUMENTS 154303  9/1985  European Pat. Off. .
685224  12/1995  European Pat. Off. .

*Primary Examiner*—Shelley A. Dodson
*Attorney, Agent, or Firm*—Norris, McLaughlin & Marcus, P.A.

[57] ABSTRACT

Light protection active ingredient combinations of tris(2-ethylhexyl) 4,4',4"-(1,3,5-triazine-2,4,6-triyltriimino) trisbenzoate and branched and/or unbranched alkanecarboxylic acids having chain lengths of from 10 to 24 carbon atoms, at least 10% of these alkanecarboxylic acids being in protonated form.

16 Claims, No Drawings

COSMETIC AND DERMATOLOGICAL SUNSCREEN FORMULATIONS CONTAINING TRIAZINE DERIVATIVES AND ALKANE CARBOXYLIC ACIDS

The present invention relates to cosmetic and dermatological light protection formulations, in particular skin care cosmetic and dermatological light protection formulations.

The damaging effect of the ultraviolet part of solar radiation on the skin is generally known. While rays having a wavelength of less than 290 nm (the UVC region) are absorbed by the ozone layer in the Earth's atmosphere, rays in the region between 290 nm and 320 nm, the UVB range, cause erythema, simple sunburn or even burns of varying severity.

The narrower region around 308 nm is stated as the erythema activity maximum of sunlight.

Numerous compounds are known for protecting against UVB radiation; these are usually derivatives of 3-benzylidenecamphor, 4-aminobenzoic acid, cinnamic acid, salicylic acid, benzophenone and also 2-phenylbenzimidazole.

For the region between about 320 nm and about 400 nm, the UVA region, it is also important to have available filter substances, since the rays of that region can also cause damage. Thus, it has been found that UVA radiation leads to damage of the elastic and collagenic fibres of connective tissue, causing premature ageing of the skin, and that it is to be regarded as a cause of numerous phototoxic and photoallergic reactions. The damaging effect of UVB radiation can be intensified by UVA radiation.

However, UV radiation can also lead to photochemical reactions, in which case the photochemical reaction products intervene in the skin's metabolism.

Such photochemical reaction products are predominantly free-radical compounds, for example hydroxyl radicals. Undefined free-radical photo-products which are formed in the skin itself can also display uncontrolled secondary reactions because of their high reactivity. However, singlet oxygen, a non-radical excited state of the oxygen molecule, can also be formed during UV irradiation, as can short-lived epoxides and many others. Singlet oxygen, for example, differs from the normal triplet oxygen (free-radical ground state) by its increased reactivity. However, excited, reactive (free-radical) triplet states of the oxygen molecule also exist.

UV radiation is also a type of ionizing radiation. There is therefore the risk that UV exposure may also produce ionic species, which then, for their part, are capable of oxidative intervention in the bio-chemical processes.

An advantageous UVB filter is tris(2-ethylhexyl) 4,4',4"-(1,3,5-triazine-2,4,6-triyltriimino)trisbenzoate, synonym: 2,4,6-tris[anilino(p-carbo-2'-ethyl-1'-hexyloxy)]-1,3,5-triazine.

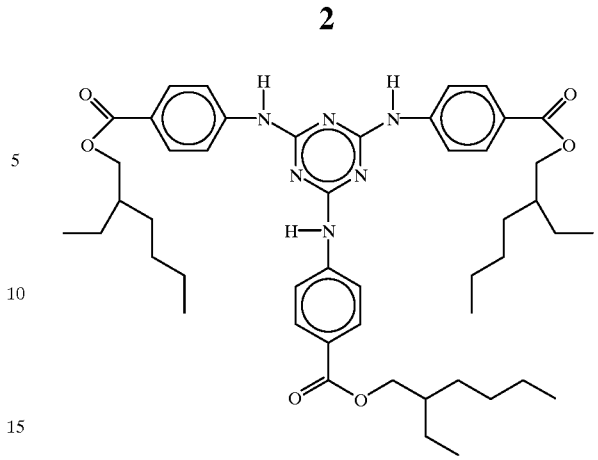

This UVB filter substance is marketed by BASF Aktiengesellschaft under the trade name UVINUL® T 150 and is distinguished by good UV absorption properties.

The main disadvantage of this UVB filter is poor solubility in lipids. Known solvents for this UVB filter can dissolve a maximum of about 15% by weight of this filter, corresponding to about 1–1.5% by weight of dissolved, and thus active, UV filter substance.

It was therefore surprising, and could not have been foreseen by the person skilled in the art, that light protection active ingredient combinations of tris(2-ethylhexyl) 4,4',4"-(1,3,5-triazine-2,4,6-triyltriimino)trisbenzoate and branched and/or unbranched alkanecarboxylic acids having chain lengths of from 10 to 24 carbon atoms, at least 10% of these alkanecarboxylic acids being in protonated form, overcome the disadvantages of the prior art.

The invention also relates in particular to the use of branched and/or unbranched alkanecarboxylic acids having chain lengths of from 10 to 24 carbon atoms, at least 10% of these alkanecarboxylic acids being in protonated form, as solvents, solubility promoters or solubilizers for tris(2-ethylhexyl) 4,4',4"-(1,3,5-triazine-2,4,6-triyltriimino) trisbenzoate, in particular for the use in light protection formulations.

A prerequisite for the suitability of the active ingredient combinations according to the invention for the purposes according to the invention is of course the cosmetic and dermatological acceptability of the base substances.

According to the invention, it is possible to double the use amounts of tris(2-ethylhexyl) 4,4',4"-(1,3,5-triazine-2,4, 6-triyltriimino)trisbenzoate in cosmetic or dermatological formulations compared with the prior art.

In addition, it was surprising that the addition of the alkanecarboxylic acids according to the invention has a stabilizing effect on solutions of tris(2-ethylhexyl) 4,4',4"-(1,3,5-triazine-2,4,6-triyltriimino)trisbenzoate, since the latter substance not only displays poor solubility, but also readily crystallizes out again from its solution. The invention thus also relates to a process for the stabilization of solutions of tris(2-ethylhexyl) 4,4',4"-(1,3,5-triazine-2,4,6-triyltriimino)trisbenzoate which is characterized in that an effective content of alkanecarboxylic acids according to the invention is added to such solutions.

Particular preference is given to those combinations which comprise, as alkanecarboxylic acids, palmitic acid and/or stearic acid and/or isostearic acid and/or eicosanoic acid.

The total amount of tris(2-ethylhexyl) 4,4',4''-(1,3,5-triazine-2,4,6-triyltriimino)trisbenzoate in the finished cosmetic or dermatological formulations is advantageously chosen from the range from 0.1–10.0% by weight, preferably 0.5–6.0% by weight, based on the total weight of the formulations.

The total amount of one or more alkanecarboxylic acids according to the invention in the finished cosmetic or dermatological preparations is advantageously chosen from the range from 0.1–10% by weight, preferably 0.5–6.0% by weight, based on the total weight of the formulations.

It is advantageous to choose weight ratios of tris(2-ethylhexyl) 4,4',4''-(1,3,5-triazine-2,4,6-tri-yltriimino) trisbenzoate and one or more alkanecarboxylic acids according to the invention from the range from 1:10 to 10:1, preferably 1:4 to 4:1.

Cosmetic and dermatological formulations according to the invention also advantageously comprise inorganic pigments consisting of metal oxides and/or other metal compounds which are sparingly soluble or insoluble in water, in particular the oxides of titanium ($TiO_2$), zinc (ZnO), iron (for example $Fe_2O_3$), zirconium ($ZrO_2$), silicon ($SiO_2$), manganese (for example MnO), aluminium ($Al_2O_3$) or cerium (for example $Ce_2O_3$), mixed oxides of the corresponding metals and mixtures of such oxides. The pigments are particularly preferably those based on $TiO_2$.

It is particularly advantageous for the purposes of the present invention, although not absolutely necessary, if the inorganic pigments are present in hydrophobic form, i.e. they have been surface-treated to repel water. This surface treatment can comprise providing the pigments with a thin hydrophobic layer by processes known per se.

Such a process comprises, for example, producing the hydrophobic surface layer by a reaction according to

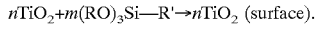

$n\text{TiO}_2 + m(\text{RO})_3\text{Si}—\text{R}' \rightarrow n\text{TiO}_2$ (surface).

n and m here are stoichiometric parameters to be employed as desired and R and R' are the desired organic radicals. Hydrophobicized pigments prepared analogously to DE-A 33 14 742, for example, are advantageous.

Advantageous $TiO_2$ pigments are obtainable, for example, under the trade names MT 100 T from TAYCA.

The cosmetic and/or dermatological light protection formulations according to the invention can have the customary composition and can be used for cosmetic and/or dermatological light protection, and furthermore for the treatment, care and cleansing of the skin and/or hair and as a make-up product in decorative cosmetics.

For use, the cosmetic and dermatological formulations according to the invention are applied to the skin and/or hair in an adequate amount in the manner customary for cosmetics.

Particularly preferred cosmetic and dermatological formulations are those which are present in the form of a sunscreen composition. These can advantageously additionally comprise at least one further UVA filter and/or at least one further UVB filter and/or at least one inorganic pigment, preferably an inorganic micropigment.

The cosmetic and dermatological formulations according to the invention can comprise cosmetic auxiliaries such as are usually used in such formulations, for example preservatives, bactericides, perfumes, antifoams, dyes, pigments which have a colouring action, thickeners, moisturizers and/or humectants, fats, oils, waxes or other customary constituents of a cosmetic or dermatological formulation, such as alcohols, polyols, polymers, foam stabilizers, electrolytes, organic solvents or silicone derivatives.

An additional content of antioxidants is generally preferred. According to the invention favourable antioxidants which can be used are all the antioxidants which are suitable or customary for cosmetic and/or dermatological uses.

The antioxidants are advantageously chosen from the group consisting of amino acids (for example glycine, histidine, tyrosine, tryptophan) and derivatives thereof, imidazoles (for example urocanic acid) and derivatives thereof, peptides, such as D,L-carnosine, D-carnosine, L-carnosine and derivatives thereof (for example anserine), carotenoids, carotenes (for example α-carotene, β-carotene, lycopene) and derivatives thereof, chlorogenic acid and derivatives thereof, lipoic acid and derivatives thereof (for example dihydrolipoic acid), aurothioglucose, propylthiouracil and other thiols (for example thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulphoximine compounds (for example buthionine-sulphoximines, homocysteine-sulphoximine, buthionine sulphones, penta-, hexa- and heptathionine-sulphoximine) in very low tolerated doses (for example pmol to $\mu$mol/kg), and furthermore (metal) chelating agents (for example α-hydroxy-fatty acids, palmitic acid, phytic acid, lactoferrin), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example γ-linolenic acid, linoleic acid, oleic acid), folic acid and derivatives thereof, furfurylidenesorbitol and derivatives thereof, ubiquinone and ubiquinol and derivatives thereof, vitamin C and derivatives (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutic acid and derivatives thereof, α-glycosylrutin, ferulic acid, furfurylideneglucitol, carnosine, butylated hydroxytoluene, butylated hydroxyanisole, nordihydroguaiac resin acid, nordihydroguaiaretic acid, trihydroxybutyrophenone, uric acid and derivatives thereof, mannose and derivatives thereof, zinc and derivatives thereof (for example ZnO, $ZnSO_4$), selenium and derivatives thereof (for example selenium methionine), stilbenes and derivatives thereof (for example stilbene oxide, trans-stilbene oxide) and the derivatives of these active ingredients mentioned which are suitable according to the invention (salts, esters, ethers, sugars, nucleotides, nucleosides, peptides and lipids).

The amount of the abovementioned antioxidants (one or more compounds) in the formulations is preferably from 0.001 to 30% by weight, particularly preferably 0.05–20% by weight, in particular 1–10% by weight, based on the total weight of the formulation.

If vitamin E and/or derivatives thereof is or are the antioxidant or antioxidants, it is advantageous to choose the respective concentrations thereof from the range 0.001–10% by weight, based on the total weight of the formulation.

If vitamin A or vitamin A derivatives or carotenes or derivatives thereof is or are the antioxidant or antioxidants, it is advantageous to choose the respective concentrations thereof from the range 0.001–10% by weight, based on the total weight of the formulation.

The lipid phase can advantageously be chosen from the following group of substances:

mineral oils, mineral waxes oils, such as triglycerides of capric or of caprylic acid, but preferably castor oil;

fats, waxes and other natural and synthetic fatty substances, preferably esters of fatty acids with alcohols of low C number, for example with isopropanol, propylene glycol or glycerol, or esters of fatty alcohols with alkanoic acids of low C number or with fatty acids;

alkyl benzoates;

silicone oils, such as dimethylpolysiloxanes, diethylpolysiloxanes, diphenylpolysiloxanes and mixed forms thereof.

If appropriate, the aqueous phase of the formulations according to the invention advantageously comprises alcohols, diols or polyols of low C number and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, furthermore alcohols of low C number, for example ethanol, isopropanol, 1,2-propanediol and glycerol, and, in particular, one or more thickeners, which can advantageously be chosen from the group consisting of silicon dioxide, aluminium silicates, polysaccharides and derivatives thereof, for example hyaluronic acid, xanthan gum and hydroxypropylmethylcellulose, particularly advantageously from the group consisting of poly-acrylates, preferably a polyacrylate from the group consisting of so-called Carbopols, for example Carbopols of types 980, 981, 1382, 2984 and 5984, in each case individually or in combination.

The cosmetic or dermatological light protection formulations advantageously comprise inorganic pigments, in particular micropigments, for example in amounts of from 0.1% by weight to 30% by weight, preferably in amounts from 0.5% by weight to 10% by weight, but in particular from 1% by weight to 6% by weight, based on the total weight of the formulations.

It is advantageous according to the invention to employ, in addition to the combinations according to the invention oil-soluble UVA filters and/or UVB filters in the lipid phase and/or water-soluble UVA filters and/or UVB filters in the aqueous phase.

The light protection formulations according to the invention can advantageously comprise further substances which absorb UV radiation in the UVB region, the total amount of filter substances being, for example, from 0.1% by weight to 30% by weight, preferably 0.5 to 10% by weight, in particular 1 to 6% by weight, based on the total weight of the formulations, in order to provide cosmetic formulations which protect the skin from the entire region of ultraviolet radiation. They can also be used as sunscreens.

The further UVB filters can be oil-soluble or water-soluble. Advantageous oil-soluble UVB filter substances are, for example:

3-benzylidenecamphor derivatives, preferably 3-(4-methylbenzylidene)camphor and 3-benzylidenecamphor;

4-aminobenzoic acid derivatives, preferably 2-ethylhexyl 4-(dimethylamino)benzoate and amyl 4-(dimethylamino)benzoate;

esters of cinnamic acid, preferably 2-ethylhexyl 4-methoxycinnamate and isopentyl 4-methoxycinnamate;

derivatives of benzophenone, preferably 2-hydroxy-4-methoxybenzophenone, 2-hydroxy-4-methoxy-4'-methylbenzophenone and 2,2'-dihydroxy-4-methoxybenzophenone;

esters of benzalmalonic acid, preferably di(2-ethylhexyl) 4-methoxybenzalmalonate.

Advantageous water-soluble UVB filter substances are, for example:

salts of 2-phenylbenzimidazole-5-sulphonic acid, such as its sodium, potassium or its triethanolammonium salt, and the sulphonic acid itself;

sulphonic acid derivatives of benzophenones, preferably 2-hydroxy-4-methoxybenzophenone-5-sulphonic acid and salts thereof;

sulphonic acid derivatives of 3-benzylidenecamphor, such as, for example, 4-(2-oxo-3-bornylidenemethyl) benzenesulphonic acid, 2-methyl-5-(2-oxo-3-bornylidenemethyl) benzenesulphonic acid and salts thereof.

The list of further UVB filters mentioned which can be used in combination with the active ingredient combinations according to the invention is not of course intended to be limiting.

It may also be advantageous to combine the combinations according to the invention with further UVA filters which have hitherto customarily been present in cosmetic formulations. These substances are preferably derivatives of dibenzoylmethane, in particular 1-(4'-tert-butylphenyl)-3-(4'-methoxyphenyl)propane-1,3-dione and 1-phenyl-3-(4'-isopropylphenyl) propane-1,3-dione. These combinations and formulations which comprise these combinations are also provided by the invention. The amounts used for the UVB combination can be employed.

It is furthermore advantageous to combine the active ingredient combinations according to the invention with further UVA and/or UVB filters.

It is also particularly advantageous to combine the active ingredient combinations according to the invention with salicylic acid derivatives, some known examples of which are likewise able to absorb UV radiation. Customary UV filters include

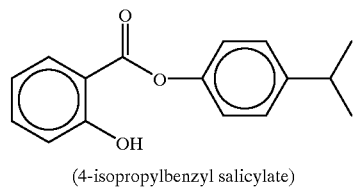

(4-isopropylbenzyl salicylate)

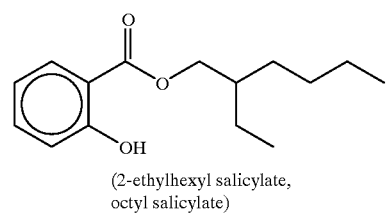

(2-ethylhexyl salicylate, octyl salicylate)

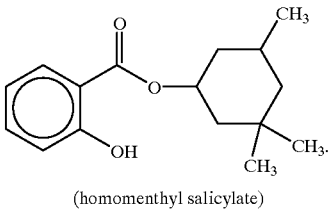

(homomenthyl salicylate)

The invention also relates to a process for the preparation of the cosmetic and/or dermatological light protection formulations according to the invention, which is characterized in that the tris(2-ethylhexyl) 4,4',4"-(1,3,5-triazine-2,4,6-triyltriimino)trisbenzoate is suspended and if desired homogenized, in a manner known per se, in one or more alkanecarboxylic acids or an oil phase containing alkanecarboxylic acids with uniform stirring and, if necessary, with warming, combined if necessary with further lipid components and if necessary with one or more emulsifiers, after which the oil phase is mixed with the aqueous phase into which, if necessary, a thickener has been incorporated, and which preferably is at roughly the same temperature as the oil phase; the mixture is homogenized if desired and left to cool to room temperature. After the mixture has cooled to room temperature, it is possible to repeat homogenization particularly if further volatile constituents are to be incorporated.

The examples below serve to illustrate the present invention without limiting it. Unless stated otherwise, all quantities, proportions and percentages are by weight and based on the total amount or on the total weight of the formulations.

EXAMPLE 1

|  | % by weight |
| --- | --- |
| Glyceryl stearate SE | 3.50 |
| Stearic acid | 1.80 |
| Glycerol | 3.00 |
| Cetearyl alcohol | 0.50 |
| Sodium hydroxide (45%) | 0.20 |
| Preservative | q.s. |
| Perfume | q.s. |
| Water, demin. | ad 100.0 |
| Octyldodecanol | 7.0 |
| Caprylyl ether | 8.0 |
| Uvinul T150 | 3.0 |
| Cetearyl isononanoate | 6.0 |
| Carbomer | 0.20 |

EXAMPLE 2

| Glyceryl stearate | 2.50 |
| --- | --- |
| Isostearic acid | 3.50 |
| Glycerol | 3.00 |
| Cetearyl alcohol | 1.50 |
| Sodium hydroxide (45%) | 0.13 |
| Octyldodecanol | 7.0 |
| Capric/caprylic triglyceride | 5.0 |
| Cetearyl isononanoate | 6.0 |
| Uvinul T150 | 5.0 |
| Carbomer | 0.2 |
| Preservative | q.s. |
| Perfume | q.s. |
| Water, demin. | ad 100.0 |

EXAMPLE 3

| Glyceryl stearate SE | 3.50 |
| --- | --- |
| Palmitic acid | 3.50 |
| Butylene glycol | 5.00 |
| Cetearyl alcohol | 3.00 |
| Sodium hydroxide (45%) | 0.35 |
| Preservative | q.s. |
| Perfume | q.s. |
| Water, demin. | ad 100.0 |
| $C_{12}$–$C_{15}$ alkyl benzoate | 10.0 |
| Uvinul T150 | 4.0 |
| Cetearyl isononanoate | 6.0 |
| Carbomer | 0.20 |

EXAMPLE 4

| Glyceryl stearate SE | 4.00 |
| --- | --- |
| Stearic acid | 2.00 |
| $C_{12}$–$C_{15}$-alkyl benzoate | 5.00 |
| Capric/caprylic triglyceride | 5.00 |
| Octyldodecanol | 5.00 |
| Butylene glycol | 5.00 |
| Cetearyl alcohol | 0.50 |
| Carbomer | 0.20 |
| Butylmethoxydibenzoyl-methane | 2.00 |
| Methylbenzylidene-camphor | 4.00 |
| Uvinul T150 | 1.00 |
| Octyl salicylate | 2.00 |
| Tocopheryl acetate | 1.00 |
| Furfurylidenesorbitol | 0.50 |
| Cyclomethicone | 2.00 |
| $Na_3$HEDTA | 1.00 |
| Sodium hydroxide (45%) | 0.25 |
| Preservative | q.s. |
| Perfume | q.s. |
| Water, demin. | ad 100.0 |

EXAMPLE 5

| Glyceryl stearate SE | 4.00 |
| --- | --- |
| Stearic acid | 2.00 |
| $C_{12}$–$C_{15}$-alkyl benzoate | 5.00 |
| Capric/caprylic triglyceride | 5.00 |
| Octyldodecanol | 5.00 |
| Glycerol | 5.00 |
| Cetearyl alcohol | 0.50 |
| Carbomer | 0.20 |
| Butylmethoxydibenzoyl-methane | 2.00 |
| Methylbenzylidene-camphor | 4.00 |
| Uvinul T150 | 1.50 |
| Octyl salicylate | 3.00 |
| Tocopheryl acetate | 1.00 |
| Furfurylidenesorbitol | 0.50 |
| Cyclomethicone | 2.00 |

-continued

| | |
|---|---|
| Na₃HEDTA | 1.00 |
| Sodium hydroxide (45%) | 0.25 |
| Preservative | q.s. |
| Perfume | q.s. |
| Water, demin. | ad 100.0 |

EXAMPLE 6

| | |
|---|---|
| Glyceryl stearate SE | 4.00 |
| Stearic acid | 2.00 |
| C₁₂–C₁₅-alkyl benzoate | 5.00 |
| Capric/caprylic triglyceride | 5.00 |
| Octyldodecanol | 5.00 |
| Butylene glycol | 5.00 |
| Cetearyl alcohol | 0.50 |
| Carbomer | 0.20 |
| Butylmethoxydibenzoyl-methane | 2.00 |
| Methylbenzylidene-camphor | 4.00 |
| Uvinul T150 | 1.50 |
| Octyl salicylate | 4.00 |
| Tocopheryl acetate | 1.00 |
| Furfurylidenesorbitol | 0.50 |
| Cyclomethicone | 2.00 |
| Na₃HEDTA | 1.00 |
| Sodium hydroxide (45%) | 0.25 |
| Preservative | q.s. |
| Perfume | q.s. |
| Water, demin. | ad 100.0 |

EXAMPLE 7

| | |
|---|---|
| Glyceryl stearate SE | 4.00 |
| Stearic acid | 2.00 |
| C₁₂–C₁₅-alkyl benzoate | 5.00 |
| Mineral oil | 5.00 |
| Octyldodecanol | 5.00 |
| Glycerol | 5.00 |
| Cetearyl alcohol | 0.50 |
| Carbomer | 0.20 |
| Butylmethoxydibenzoyl-methane | 2.00 |
| Methylbenzylidene-camphor | 4.00 |
| Uvinul T150 | 1.50 |
| Octyl salicylate | 5.00 |
| Tocopheryl acetate | 1.00 |
| Furfurylidenesorbitol | 0.50 |
| Cyclomethicone | 2.00 |
| Na₃HEDTA | 1.00 |
| Sodium hydroxide (45%) | 0.25 |
| Preservative | q.s. |
| Perfume | q.s. |
| Water, demin. | ad 100.0 |

EXAMPLE 8

| | |
|---|---|
| Glyceryl stearate SE | 4.00 |
| Stearic acid | 2.00 |
| C₁₂–C₁₅-alkyl benzoate | 5.00 |
| Capric/caprylic triglyceride | 5.00 |
| Octyldodecanol | 5.00 |

-continued

| | |
|---|---|
| Butylene glycol | 5.00 |
| Cetearyl alcohol | 0.50 |
| Carbomer | 0.20 |
| Butylmethoxydibenzoyl-methane | 2.00 |
| Methylbenzylidene-camphor | 4.00 |
| Uvinul T150 | 2.00 |
| Octyl salicylate | 5.00 |
| Tocopheryl acetate | 1.00 |
| Furfurylidenesorbitol | 0.50 |
| Cyclomethicone | 2.00 |
| Na₃HEDTA | 1.00 |
| Sodium hydroxide (45%) | 0.25 |
| Preservative | q.s. |
| Perfume | q.s. |
| Water, demin. | ad 100.0 |

EXAMPLE 9

| | |
|---|---|
| Glyceryl stearate SE | 4.00 |
| Stearic acid | 2.00 |
| C₁₂–C₁₅-alkyl benzoate | 5.00 |
| Capric/caprylic triglyceride | 5.00 |
| Octyldodecanol | 5.00 |
| Butylene glycol | 5.00 |
| Cetearyl alcohol | 0.50 |
| Carbomer | 0.20 |
| Butylmethoxydibenzoyl-methane | 2.00 |
| Methylbenzylidene-camphor | 4.00 |
| Uvinul T150 | 2.00 |
| Octyl salicylate | 5.00 |
| Homomenthyl salicylate | 5.00 |
| Tocopheryl acetate | 1.00 |
| Furfurylidenesorbitol | 0.50 |
| Cyclomethicone | 2.00 |
| Na₃HEDTA | 1.00 |
| Sodium hydroxide (45%) | 0.25 |
| Preservative | q.s. |
| Perfume | q.s. |
| Water, demin. | ad 100.0 |

We claim:

1. A cosmetic or dermatologic composition comprising an amount effective to protect skin against the damaging effects of UV light of a combination of:
 a) tris (2-ethylhexyl) 4,4',4"-(1,3,5-triazine-2,4,6-triyltriimino) trisbenzoate; and
 b) one or more branched alkanecarboxylic acids having chain lengths from 10 to 24 carbon atoms, at least 10% of said alkanecarboxylic acids being in protonated form.

2. A cosmetic or dermatologic composition according to claim 1, which further comprises a salicylic acid derivative selected from the group consisting of 4-isopropylbenzyl salicylate, 2-ethylhexyl salicylate, octyl salicylate, homomenthyl salicylate and mixtures thereof.

3. A cosmetic or dermatologic composition according to claim 1, which comprises tris (2-ethylhexyl) 4,4',4"-(1,3,5-triazine-2,4,6-triyltriimino) trisbenzoate in an amount ranging from 0.1–10.0% by weight based on the total weight of the composition.

4. A cosmetic or dermatologic composition according to claim 3, which comprises tris (2-ethylhexyl) 4,4',4"-(1,3,5-triazine-2,4,6-triyltriimino) trisbenzoate in an amount ranging from 0.5–6.0% by weight based on the total weight of the composition.

5. A cosmetic or dermatologic composition according to claim 1, which comprises one or more branched alkanecarboxylic acids having chain lengths from 10 to 24 carbon atoms in an amount ranging from 0.1–10.0% by weight based on the total weight of the composition.

6. A cosmetic or dermatologic composition according to claim 5, which comprises one or more branched alkanecarboxylic acids having chain lengths from 10 to 24 carbon atoms in an amount ranging from 0.5–6.0% by weight based on the total weight of the composition.

7. A cosmetic or dermatologic composition according to claim 1, which comprises:
   a) tris (2-ethylhexyl) 4,4',4"-(1,3,5-triazine-2,4,6-triyltriimino) trisbenzoate; and
   b) one or more branched alkanecarboxylic acids having chain lengths from 10 to 24 carbon atoms;
   in a weight ratio of a):b) ranging from 1:10 to 10:1.

8. A cosmetic or dermatologic composition according to claim 7, wherein the ratio of a):b) ranges from 1:4 to 4:1.

9. A method of protecting skin from the damaging effects of UV light comprising applying thereto a cosmetic or dermatologic composition comprising an amount effective to protect skin against the damaging effects of UV light of a combination of:
   a) tris (2-ethylhexyl) 4,4',4"-(1,3,5-triazine-2,4,6-triyltriimino) trisbenzoate; and
   b) one or more branched alkanecarboxylic acids having chain lengths from 10 to 24 carbon atoms, at least 10% of said alkanecarboxylic acids being in protonated form.

10. The method according to claim 9, wherein said cosmetic or dermatologic composition further comprises a salicylic acid derivative selected from the group consisting of 4-isopropylbenzyl salicylate, 2-ethylhexyl salicylate, octyl salicylate, homomenthyl salicylate and mixtures thereof.

11. The method according to claim 9, wherein said cosmetic or dermatologic composition comprises tris (2-ethylhexyl) 4,4',4"-(1,3,5-triazine-2,4,6-triyltriimino) trisbenzoate in an amount ranging from 0.1–10.0% by weight based on the total weight of the composition.

12. The method according to claim 11, wherein said cosmetic or dermatologic composition comprises tris (2-ethylhexyl) 4,4',4"-(1,3,5-triazine-2,4,6-triyltriimino) trisbenzoate in an amount ranging from 0.5–6.0% by weight based on the total weight of the composition.

13. The method according to claim 9, wherein said cosmetic or dermatologic composition comprises one or more branched alkanecarboxylic acids having chain lengths from 10 to 24 carbon atoms in an amount ranging from 0.1–10.0% by weight based on the total weight of the composition.

14. The method according to claim 13, wherein said cosmetic or dermatologic composition comprises one or more branched alkanecarboxylic acids having chain lengths from 10 to 24 carbon atoms in an amount ranging from 0.5–6.0% by weight based on the total weight of the composition.

15. The method according to claim 9, wherein said cosmetic or dermatologic composition comprises:
   a) tris (2-ethylhexyl) 4,4',4"-(1,3,5-triazine-2,4,6-triyltriimino) trisbenzoate; and
   b) one or more branched alkanecarboxylic acids having chain lengths from 10 to 24 carbon atoms;
   in a weight ratio of a):b) ranging from 1:10 to 10:1.

16. The method according to claim 15, wherein in said cosmetic or dermatologic composition the ratio of a):b) ranges from 1:4 to 4:1.

* * * * *